United States Patent
Wood

(10) Patent No.: US 6,448,262 B1
(45) Date of Patent: Sep. 10, 2002

(54) PESTICIDAL AND PARASITICIDAL USE OF 2-(SUBSTITUTED THIO) THIAZOLO-[4,5-B] PYRIDINE COMPOUNDS

(75) Inventor: William Wakefield Wood, Pennington, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/435,342

(22) Filed: Nov. 5, 1999

Related U.S. Application Data

(60) Provisional application No. 60/198,595, filed on Nov. 16, 1998.

(51) Int. Cl.[7] .................. A01N 43/90; C07D 513/04
(52) U.S. Cl. ....................................... 514/301; 546/114
(58) Field of Search ........................... 546/114; 514/301

(56) References Cited

U.S. PATENT DOCUMENTS

| | | | |
|---|---|---|---|
| 4,477,276 A | 10/1984 | Willims et al. .............. 71/94 |
| 5,079,255 A | 1/1992 | Katano et al. .............. 514/303 |
| 5,451,594 A | 9/1995 | Fitzjohn et al. ............. 514/594 |
| 5,728,833 A | 3/1998 | Turnbull et al. ............ 544/309 |

FOREIGN PATENT DOCUMENTS

| | | |
|---|---|---|
| EP | 342150 A1 | 11/1989 |
| EP | 4100551 A1 | 1/1991 |
| EP | 507464 A1 | 10/1992 |
| EP | 405976 B1 | 4/1995 |
| GB | 2293380 A | 3/1996 |
| WO | 94/06782 | 3/1994 |
| WO | 9406783 | 3/1994 |

OTHER PUBLICATIONS

Smith et al., "A Convenient Synthesis of 2–Substituted Thiazolo [4,5–b]pyridines via Directed Metalation", Sulfur Letters, vol. 18(2) 1995, pp. 79–95.
K. Smith et al. Sulfur Letters, 18(2), pp. 79095 (1995).

Primary Examiner—Patricia L. Morris
(74) Attorney, Agent, or Firm—Keil & Weinkauf

(57) ABSTRACT

The present invention relates to the pesticidal and parasiticidal use of 2-(substituted thio)thiazolo[4,5-b]pyridine compounds having the structural formula I

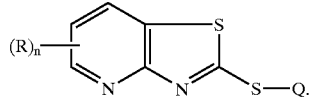

8 Claims, No Drawings

PESTICIDAL AND PARASITICIDAL USE OF 2-(SUBSTITUTED THIO) THIAZOLO-[4,5-B] PYRIDINE COMPOUNDS

This application contains benefit of priority of provisional application Ser. No. 60/198,595, filed Nov. 16, 1998.

BACKGROUND OF THE INVENTION

Nematode, insect and acarid pests destroy growing and harvested crops. In the United States, agronomic crops must compete with thousands of those pests. In addition, arthropod and helminth parasites cause hundreds of millions of dollars in economic damage to the livestock and companion animal sectors annually on a global basis. Arthropod parasites also are a nuisance to humans and can vector disease causing organisms in humans and animals.

In spite of the commercial pesticides, ectoparasiticides, endectocides and anthelmintics available today, damage to crops, livestock, companion animals and humans still occurs. Accordingly, there is ongoing research to create new and more effective pesticides, ectoparasiticides, endectocides and anthelmintics.

Certain azole derivatives which are useful as anti-ulcer agents are described in EP 405976-B1. However, that patent does not describe or suggest any pesticidal or parasiticidal utility for the azole derivatives described therein.

It is, therefore, an object of the present invention to provide a method for the control of helminth, nematode, insect and acarid pests and parasites.

It is also an object of the present invention to provide a method for the protection of growing and harvested crops from damage caused by nematode, insect and acarid attack and infestation.

It is a further object of this invention to provide a method for treating, controlling, preventing and protecting warm-blooded animals, fish and humans against infestation and infection by helminths, acarids and arthropod endo- and ectoparasites.

These and other objects of the present invention will become more apparent from the description thereof set forth below.

SUMMARY OF THE INVENTION

The present invention provides a method for the control of helminth, nematode, insect or acarid pests or parasites which comprises contacting said pests or parasites or their food supply, habitat or breeding grounds with a pesticidally or parasiticidally effective amount of a 2-(substituted thio) thiazolo[4,5-b]pyridine compound having the structural formula I

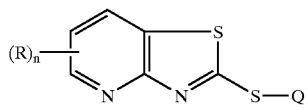

wherein

R is halogen, nitro, cyano, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio or $CO_2R_1$;

n is 0, 1, 2 or 3;

Q is $C_3$–$C_6$alkenyl, $C_3$–$C_6$haloalkenyl, $C_3$–$C_7$cycloalkyl, $C_3$–$C_7$halocycloalkyl, $C_4$–$C_7$cycloalkenyl, $C_4$–$C_7$halocycloalkenyl, $C_1$–$C_6$alkyl optionally substituted with one $C_3$–$C_7$cycloalkyl, $C_3$–$C_7$halocycloalkyl or $CO_2R_2$ group, $C_1$–$C_6$haloalkyl optionally substituted with one $C_3$–$C_7$cycloalkyl, $C_3$–$C_7$halocycloalkyl or $CO_2R_2$ group; and $R_1$ and $R_2$ are each independently hydrogen, $C_1$–$C_6$alkyl, $CH_2(C_1$–$C_6$haloalkyl), $C_3$–$C_{10}$alkenyl, $C_3$–$C_{10}$haloalkenyl, a cation, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups; and the agriculturally and/or pharmaceutically acceptable salts thereof.

This invention also comprises pesticidal and parasiticidal compositions containing those compounds. Advantageously, it has been found that the 2-(substituted thio)thiazolo[4,5-b]pyridine compounds, and compositions containing them, are especially useful for the control of nematode pests.

DETAILED DESCRIPTION OF THE INVENTION

The present invention provides a method for the control of helminth, nematode, insect or acarid pests or parasites which comprises contacting said pests or parasites or their food supply, habitat or breeding grounds with a pesticidally or parasiticidally effective amount of a 2-(substituted thio) thiazolo[4,5-b]pyridine compound of formula I.

Formula I compounds which are especially useful for the control of nematodes include
2-[(4,4,3-trifluoro-3-butenyl)thio]thiazolo[4,5-b]pyridine;
2-[(bromodifluoromethyl)thio]thiazolo[4,5-b]pyridine; and
2-[(difluoromethyl)thio]thiazolo[4,5-b]pyridine, among others.

The present invention also provides a method for the protection of growing plants from attack or infestation by nematode, insect or acarid pests which comprises applying to the foliage of the plants, or to the soil or water in which they are growing, a pesticidally effective amount of a 2-(substituted thio)thiazolo[4,5-b]pyridine compound of formula I.

The formula I compounds of this invention are useful for the control of plant parasitic nematodes and nematodes living freely in soil. Plant parasitic nematodes include, but are not limited to, ectoparasites such as Xiphinema spp., Longidorus spp. and Trichodorus spp.; semi-parasites such as Tylenchulus spp.; migratory endoparasites such as Pratylenchus spp., Radopholus spp. and Scutellonema spp.; sedentary parasites such as Heterodera spp., Globodera spp. and Meloidogyne spp.; and stem and leaf endoparasites such as Ditylenchus spp., Aphelenchoides spp. and Hirshmaniella spp.

The 2-(substituted thio)thiazolo[4,5-b]pyridine compounds of formula I are also useful for controlling insect and/or acarid pests. Insects controlled by the formula I compounds of this invention include, but are not limited to, Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the formula I compounds of this invention include, but are not limited to, mites such as two-spotted spider mites, carmine spider mites, banks grass mites, strawberry mites, citrus rust mites and leprosis mites.

In practice generally about 0.1 ppm to about 10,000 ppm and preferably about 1 ppm to about 5,000 ppm of a formula I compound, dispersed in water or another liquid carrier, is effective when applied to plants or the soil or water in which the plants are growing or are to be grown to protect the plants from nematode, insect and/or acarid attack and infestation.

The 2-(substituted thio)thiazolo[4,5-b]pyridine compounds are also effective for controlling nematode, insect and/or acarid pests when applied to the foliage of plants and/or to the soil or water in which said plants are growing or are to be grown in sufficient amount to provide a rate of about 0.1 kg/ha to 4.0 kg/ha of active ingredient.

While the formula I compounds of this invention are effective for controlling nematode, insect and/or acarid pests of agronomic crops, both growing and harvested, when employed alone, they may also be used in combination with other biological agents used in agriculture, including, but no limited to, other nematicides, insecticides and/or acaricides. For example, the formula I compounds of this invention may be used effectively in conjunction or combination with pyrethroids, phosphates, carbamates, cyclodienes, endotoxin of *Bacillus thuringiensis* (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a formula I compound of this invention (or combinations thereof) admixed with one or more agronomically acceptable inert, solid or liquid carriers. Those compositions contain a pesticidally effective amount of said compound or compounds, which amount may vary depending upon the particular compound, target pest, and method of use. Those skilled in the art can readily determine what is a pesticidally effective amount without undue experimentation.

This invention also provides a method for treating, controlling, preventing and protecting warm-blooded animals, including humans, and fish against infestation and infection by helminths, acarids and arthropod endo- and ectoparasites which comprises orally, topically or parenterally administering or applying to said animals an anthelmintically, acaricidally or endo- or ectoparasiticidally effective amount of a 2-(substituted thio)thiazolo[4,5-b] pyridine compound of formula I.

The above method is particularly useful for controlling and preventing helminth, acarid and arthropod endo- and ectoparasitic infestations and infections in warm-blooded animals such as cattle, sheep, swine, camels, deer, horses, poultry, fish, rabbits, goats, dogs and cats as well as humans.

Helminthias is a widespread disease found in many farm and companion animals and is responsible for significant economic losses throughout the world. Among the helminths causing significant damage are members of the class Trematoda, commonly known as flukes or flatworms, especially members of the genera Fasciola, Fascioloides, Paramphistomum, Dicrocoelium, Eurytrema, Ophisthorchis, Fasciolopsis, Echinostoma and Paragonimus. Helminthiases is also caused by a group of worms referred to as nematodes. Nematodes cause serious damage to the walls and tissues of the organs in which they reside, including the intestinal tract, heart, lungs and blood vessels, and are a primary cause of anemia. If left untreated they may result in death to the infected animals. The nematodes most commonly found to be the infecting agents of warm-blooded animals include members of the genera Haemonchus, Ostertagia, Cooperia, Oesphagastomum, Nematodirus, Dictyocaulus, Trichuris, Dirofilaria, Ancyclostoma, Ascaris and the like. Advantageously, the formula I compounds of this invention are useful against the causative agents of helminthiases.

Besides controlling helminths, the formula I compounds of this invention control endoparasitic arthropod infestations such as cattle grub and stomach bot. In addition, acarid and arthropod ectoparasitic infestations in warm-blooded animals and fish including, but not limited to, lice, mites, ticks, nasal bots, keds, biting flies, muscoid flies, flies, myiasitic fly larvae, chiggers, gnats, mosquitoes and fleas may be controlled, prevented or eliminated by the 2-(substituted thio)thiazolo[4,5-b]pyridine compounds of this invention. The formula I compounds of this invention may also be used to control mites which are parasitic on warm-blooded mammals and poultry including mites of the orders Acariformes and Parasitiformes. Arthropod ectoparasites which may be controlled by the formula I compounds of this invention include, but are not limited to, biting lice, sucking lice, bot flies, biting flies, gnats, mosquitoes and fleas. Biting lice include members of Mallophaga such as *Bovicola bovis*, *Trichodectes canis* and *Damilina ovis*. Sucking lice include members of Anoplura such as *Haematopinus eurysternus*, *Haematopinus suis, Linognathus vituli* and *Solenopotes capillatus*. Biting flies include members of Haematobia.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with about 0.01 mg/kg to 100 mg/kg of animal body weight per day of the formula I compound.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with about 0.01 mg/kg to 100 mg/kg of animal body weight per day of the formula I compound.

The formula I compounds may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the formula I compound. In addition, the formula I compounds may be formulated as ear tags for animals, particularly quadrupeds such as cattle and sheep.

The formula I compounds of this invention may also be used in combination or conjunction with one or more other parasiticidal compounds including, but not limited to, anthelmintics, such as benzimidazoles, piperazine, levamisole, pyrantel, praziquantel and the like; endectocides such as avermectins, milbemycins and the like; ectoparasiticides such as arylpyrroles, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

The formula I compounds may also be used in combination or conjunction with one or more conventional synergists such as piperonyl butoxide, N-octyl bicycloheptene dicarboximide, dipropyl pyridine-2,5-dicarboxylate and 1,5a,6,9,9a,9b-hexahydro-4a(4H)-dibenzofurancarboxaldehyde to enhance efficacy, broaden spectrum and provide a convenient method for parasite control.

The parasiticidal compositions of the present invention include a formula I compound of this invention (or combinations thereof) admixed with one or more pharmaceutically and/or agronomically acceptable inert, solid or liquid carriers. Those compositions contain a parasiticidally effective amount of said compound or compounds. Those skilled in the art can readily determine what is a parasiticidally effective amount without undue experimentation.

The present invention also provides novel 2-(substituted thio)thiazolo[4,5-b]pyridine compounds having the structural formula Ia

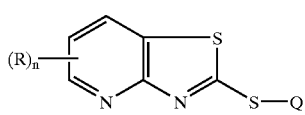
(Ia)

wherein

R is halogen, nitro, cyano, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio or $CO_2R_1$;

n is 0, 1, 2 or 3;

Q is $C_3$–$C_6$haloalkenyl, $C_3$–$C_7$cycloalkyl, $C_3$–$C_7$halocycloalkyl, $C_4$–$C_7$cycloalkenyl, $C_4$–$C_7$halocycloalkenyl,
$C_1$–$C_6$alkyl substituted with one $C_3$–$C_7$cycloalkyl or $C_3$–$C_7$halocycloalkyl group, or
$C_1$–$C_6$haloalkyl optionally substituted with one $C_3$–$C_7$cycloalkyl or $C_3$–$C_7$halocycloalkyl group,
provided that Q is other than $CF_2H$; and $R_1$ is hydrogen, $C_1$–$C_6$alkyl, $CH_2(C_1$–$C_6$haloalkyl), $C_3$–$C_{10}$alkenyl, $C_3$–$C_{10}$haloalkenyl, a cation,
benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups; and the agriculturally and/or pharmaceutically acceptable salts thereof.

In addition, the present invention provides 2[(difluoromethyl)thio]thiazolo[4,5-b]pyridine.

Exemplary of halogen hereinabove are fluorine, chlorine, bromine and iodine. The terms "$C_1$–$C_4$haloalkyl", "$C_1$–$C_6$haloalkyl, "$C_1$–$C_4$haloalkoxy", "$C_1$–$C_4$haloalkylthio", "$C_3$–$C_7$halocycloalkyl", "$C_3$–$C_6$haloalkenyl", "$C_3$–$C_{10}$haloalkenyl" and "$C_4$–$C_7$halocycloalkenyl" are defined as a $C_1$–$C_4$alkyl group, a $C_1$–$C_6$alkyl group, a $C_1$–$C_4$alkoxy group, a $C_1$–$C_4$alkylthio group, a $C_3$–$C_7$cycloalkyl group, a $C_3$–$C_6$alkenyl group, a $C_3$–$C_{10}$alkenyl group and a $C_4$–$C_7$cycloalkenyl group substituted with one or more halogen atoms, respectively. As used in formulas I and Ia above, cation designates alkali metals, alkaline earth metals, manganese, copper, iron, zinc, cobalt, lead, silver, nickel, ammonium or organic ammonium. Alkali metals include sodium, potassium and lithium. Alkaline earth metals include calcium and magnesium. Organic ammonium cations include, but are not limited to, monoalkylammonium, dialkylammonium, trialkylammonium, tetraalkylammonium, monoalkenylammonium, dialkenylammonium, trialkenylammonium, monoalkynylammonium, dialkynylammonium, monoalkanolammonium, dialkanolammonium, $C_5$–$C_6$cycloalkylammonium, piperidinium, morpholinium, pyrrolidinium, benzylammonium and the like.

The formula I compounds of this invention may be prepared by reacting a 2-thiolthiazolo[4,5-b]pyridine compound having the structural formula II with an electrophile compound having the structural formula III and a base in the presence of a solvent as shown below in Flow Diagram I.

FLOW DIAGRAM I

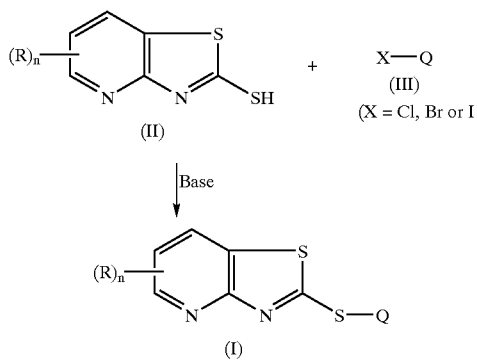

In addition, certain compounds of formula I may be converted into other compounds of formula I by using conventional procedures known to those skilled in the art.

Starting compounds of formula II are known in the art and may be prepared by the procedures described by K. Smith et al in Sulfur Letters, 18(2), pages 79–95 (1995).

In order to facilitate a further understanding of the invention, the following examples are presented to illustrate more specific details thereof. The invention is not to be limited thereby except as defined in the claims.

EXAMPLES 1–6

Preparation of 2-[(4,4,3-Trifluoro-3-butenyl)thio]thiazolo[4,5-b]pyridine

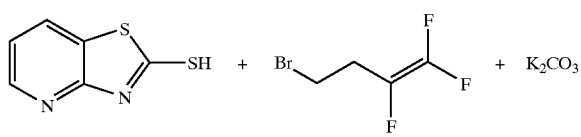

-continued

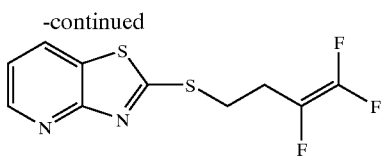

A solution of thiazolo[4,5-b]pyridine-2-thiol (6.2 g, 0.037 mol) in N,N-dimethylformamide under nitrogen is treated with 1,1,2-trifluoro-4-bromobutene (8.3 g, 0.046 mol) and potassium carbonate (1.5 g), heated to and stirred at 60° C. for 24 hours, cooled, and poured into water. The resultant aqueous mixture is extracted with diethyl ether. The organic extract is dried over anhydrous sodium sulfate and concentrated in vacuo to obtain a residue. Column chromatography of the residue using silica gel and a 9:1 hexanes/ethyl acetate solution gives the title product as a colorless oil (8.9 g, 64% yield).

$C_{10}H_7F_3N_2S_2$ Calculated: C, 43.47; H, 2.55; N, 10.14%. Found: C, 43.46; H, 2.58; N, 10.14%.

Using essentially the same procedure as described in example 1, the following compounds are obtained:

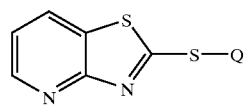

| Example | Q | Color/State | mp ° C. | | Elemental Analysis C % | H % | N % |
|---|---|---|---|---|---|---|---|
| 2 | $CH_2CH{=}CH_2$ | Red liquid | | Calc. | 51.90 | 3.87 | 13.45 |
| | | | | Found | 52.22 | 3.94 | 13.18 |
| 3 | $CH_2{-}\triangleleft$ | Lt. Yellow solid | 39.5–42.0 | Calc. | 54.02 | 4.53 | 12.60 |
| | | | | Found | 54.24 | 5.39 | 12.51 |
| 4 | $CH_2CO_2CH_3$ | White solid | 68–71 | Calc. | 44.98 | 3.36 | 11.66 |
| | | | | Found | 44.93 | 3.54 | 11.63 |
| 5 | $CH_2CO_2C_2H_5$ | White solid | 70–72 | Calc. | 47.23 | 3.96 | 11.01 |
| | | | | Found | 47.52 | 4.18 | 10.82 |
| 6 | $CH(CH_3)CO_2C_2H_5$ | Lt. yellow liquid | | Calc. | 49.23 | 4.51 | 10.44 |
| | | | | Found | 49.50 | 4.61 | 10.38 |

EXAMPLE 7

Preparation of 2-[(Bromodifluoromethyl)thio]thiazolo[4,5-b]pyridine

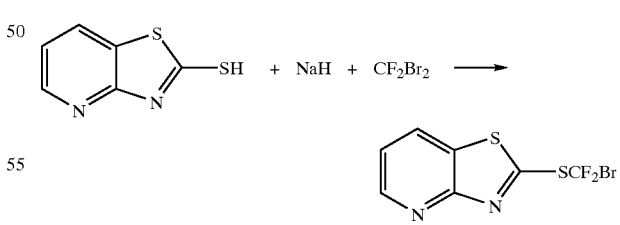

A solution of thiazolo[4,5-b]pyridine-2-thiol (2.0 g, 12 mol) in N,N-dimethylformamide is added dropwise to a mixture of sodium hydride (0.96 g, 0.024 mol) in N,N-dimethylformamide over 30 minutes. The resultant reaction mixture is treated with a solution of dibromodifluoromethane (2.52 g) in N,N-dimethylformamide, stirred at room temperature for 24 hours, and poured into an ice-water mixture. The resultant aqueous mixture is extracted with ethyl acetate. The organic extract is washed with brine, dried over anhydrous sodium sulfate, and concentrated in vacuo to obtain a residue. Chromatography of the residue using silica gel and dichloromethane followed by azeotropic removal of N,N-dimethylformamide (toluene) affords an oil. The oil is further purified by column chromatography using silica gel and a 20:1 ethyl acetate/hexanes solution to give the title product as a light yellow liquid (0.61 g, 17% yield).

EXAMPLE 8

Preparation of 2-[(Difluoromethyl)thio]thiazolo[4,5-b]pyridine

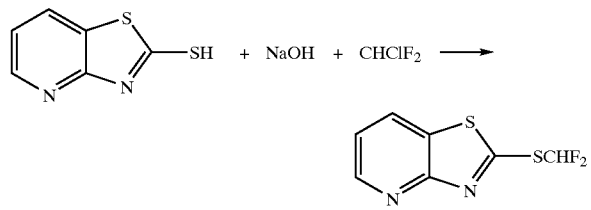

A solution of thiazolo[4,5-b]pyridine-2-thiol (2.0 g, 12 mmol) in dioxane is treated with a solution of sodium hydroxide (4.8 g, 120 mmol) in water, heated to 70° C., treated with a steady stream of chlorodifluoromethane for 75 minutes, and poured onto ice. The resultant aqueous mixture is acidified with concentrated hydrochloric acid and extracted with dichloromethane. The organic extract is dried over anhydrous sodium sulfate and concentrated in vacuo to obtain a residue. Column chromatography of the residue using silica gel and several ethyl acetate/hexanes solutions gives the title product as a light yellow solid (0.86 g, 33% yield, mp 41–43° C.).

$C_7H_4F_2N_2S_2$ Calculated: C, 38.52; H, 1.85; N, 12.84%. Found: C, 38.58; H, 1.73; N, 12.72%.

EXAMPLE 9

Preparation of 2-[(2,2,2-Trifluoroethyl)thio]thiazolo[4,5-b]pyridine

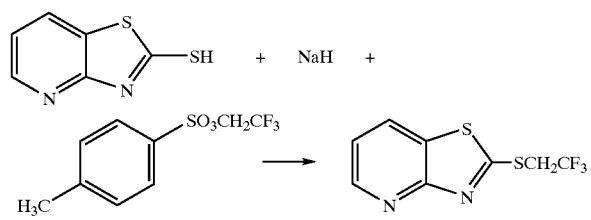

A mixture of sodium hydride (60% suspension in oil, 0.72 g, 0.03 mol) in N,N-dimethylformamide is cooled to 0° C., treated dropwise with a solution of thiazolo[4,5-b]pyridine-2-thiol (5.0 g, 30 mmol) in N,N-dimethylformamide, stirred for 30 minutes, treated with a solution of 2,2,2-trifluoroethyl p-toluenesulfonate (3.81 g, 15 mmol) in N,N-dimethylformamide, heated to and stirred at 110° C. for 6 hours, and poured into an ice/water mixture. The resultant aqueous mixture is extracted with diethyl ether. The organic extract is washed with water, dried over anhydrous sodium sulfate, and concentrated in vacuo to obtain a residue. Column chromatography of the residue using an ethyl acetate/hexanes solution gives the title product as a light yellow liquid (2.91 g, 39% yield).

$C_8H_5F_3N_2S_2$ Calculated: C, 38.39; H, 2.01; N, 11.19%. Found: C, 38.58; H, 2.08; N, 10.94%.

EXAMPLE 10

Soil Nematicide Assay Targeting Root-knot Nematode, *Meloidogyne incognita* on Potted Tomato The test compound is solubilized in acetone and diluted with water to the required test concentration. Silty loam soil in a 3 inch pot with a 3-week-old tomato transplant is drenched with the test solution. Four thousand root-knot nematode *Meloidogyne incognita* J2 larvae are dispensed in a aqueous suspension onto the soil. The pots are kept in the greenhouse and 4 weeks following inoculation of the pots, plant roots are washed free of soil and scored for the degree of root galling using the root-knot galling index identified below. Ethoprophos is included in the test as an industrial standard. The results are summarized in Table I.

| Root-Knot Galling Index | |
|---|---|
| Galling Index | Percentage of total root system galled |
| 0 | 0 |
| 1 | 10 |
| 2 | 20 |
| 3 | 30 |
| 4 | 40 |
| 5 | 50 |
| 6 | 60 |
| 7 | 70 |
| 8 | 80 |
| 9 | 90 |
| 10 | 100 |

TABLE I

| Soil Nematicide Evaluations | | |
|---|---|---|
| Compound | Rate (ppm) | Galling Index |
| Example 1 | 50 | 0[1] |
|  | 25 | 0[1] |
|  | 10 | 0 |
| Ethoprophos | 50 | 0[1] |
|  | 25 | 0[1] |
|  | 10 | 0 |
| Check | — | 7 |

[1]Phytotoxicity observed

EXAMPLE 11

Evaluation of Test Compounds Against *C. elegans*

Cultures of *C. elegans* (Bristol strain from J. Lewis) are maintained on *E. coli* lawns on NG Agar Plates at 20 20 C. New cultures are established weekly. Nematodes for testing are washed from cultures using Na buffer. Compounds are dissolved in 80% acetone. The test material is micropipetted (25 µl) into a single well of a 96-well sterile tissue culture plate and the solvent allowed to evaporate. A freshly prepared volume (50 µl) of *C. elegans* in Na buffer is micropipetted into each treated well and several control wells per plate. Plates are incubated at 20° C. Observations for efficacy are made under a dissecting microscope at 4 and 24 hours post-immersion. Immediately prior to reading the plate, it is gently tapped to stimulate the movement of the worms. Activity is judged subjectively, but semi-quantitatively, based on the drug effects on motility of the adults and larvae. The criteria are as follows: 9=complete kill in 4 hours, 8=complete kill in 24 hours, 7=markedly reduced motility in approximately 95% of worms in 24 hours, and 0=normal motility, same as controls. The results are summarized in Table II.

TABLE II

Evaluation of Test Compounds against *C. elegans*

| Example | *C. elegans* (300 ppm) |
|---|---|
| 1 | 7 |
| 2 | 0 |
| 3 | 9 |
| 4 | 9 |
| 5 | 9 |
| 6 | 9 |

EXAMPLE 12

Insecticidal and Acaricidal Evaluation of Test Compounds

Test solutions are prepared by dissolving the test compound in a 35% acetone in water mixture to give a concentration of 10,000 ppm. Subsequent dilutions are made with water as needed.

*Spodoptera eridania,* 2nd Instar Larvae, Southern Armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 2nd instar caterpillars. At 5 days, observations are made of mortality, reduced feeding, or any interference with normal molting.

*Diabrotica virgifera virgifera* Leconte, 2nd Instar Western Corn Rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 2nd instar rootworms are added to each jar and the jars are loosely capped to allow air exchange for the larvae. The treatments are held for 5 days when mortality counts are made. Missing larvae are presumed dead, since they decompose rapidly and cannot be found. The concentrations of active ingredient used in this test correspond approximately to 50 kg/ha.

*Tetranychus urticae* (OP-resistant Strain), 2-spotted Spider Mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

*Aphis gossypii,* Cotton Aphid (CA)

Cotton plants at the cotyledon stage are selected and cut back to one plant per pot. A heavily infested leaf is taken from the main colony and placed on top of each cotyledon. The aphids are allowed to transfer to the host plant overnight. At the time of test treatment, the leaf used to transfer the aphids is removed and discarded. The cotyledons are dipped in the test solution and allowed to dry. After 5 days, mortality counts are made.

*Spodoptera eridania,* Eggs-southern Armyworm and *Diabrotica undecimpunctata howardi,* Eggs-southern Corn Rootworm (SAW-Eggs) and (SCR-Eggs)

Wells containing artificial diet are treated with the test solutions and dried. The appropriate insect eggs are then placed in the wells. The wells are covered with vented, adhesive, clear plastic covers. After 7 days, mortality counts are made.

The tests are rated according to the scale shown below and the data obtained are shown in Table III.

TABLE III

Insecticidal and Acaricidal Evaluations

| Ex. | CA (300[1]) | SAW (300[1]) | SAW Eggs (3000[1]) | SCR Eggs (1000[1]) | TSM (300[1]) | WCR (50[1]) |
|---|---|---|---|---|---|---|
| 1 | 0 | 0 | 8 | 9 | 0 | 0 |
| 2 | 0 | 0 | 0 | 0 | 0 | 1 |
| 3 | 4 | 0 | 0 | 0 | 0 | 0 |
| 4 | 0 | 0 | 0 | 0 | 0 | 0 |
| 5 | 0 | 0 |   | 0 | 0 | 0 |
| 6 | 0 | 0 | 9 | 0 | 0 | 0 |
| 7 | 0 | 0 | 9 | 9 | 5 | 9 |
| 8 | 3 | 0 | 9 | 9 | 8 | 9 |
| 9 | 0 | 0 | 9 | 9 | 0 | 0 |

[1]rates in ppm

EXAMPLE 13

Ectoparasiticide Evaluation of Test Compounds in *Lucilia serricata*

The test compound is dissolved in acetone to a concentration of 100 ppm. 200 μL is added to three 12 mm filter paper disks in 128 well assay trays and allowed to dry. Approximately 20 first instar blowfly larvae and 200 μL bovine serum are added to the disks. Wells are covered with plastic lids and incubated at about 27° C. Mortality is determined at 24 and 48 hours. The results are summarized in Table IV.

TABLE IV

Evaluation of Test Compounds against *Lucilia serricata*

| | | Percent Mortality | |
|---|---|---|---|
| Example | Rate (ppm) | 24 hr | 48 hr |
| 1 | 100 | 100 | 100 |
| 2 | 100 | 0 | 0 |
| 3 | 100 | 0 | 0 |
| 6 | 100 | 0 | 0 |
| 7 | 100 | 80 | 100 |
| 8 | 100 | 0 | 0 |
| 9 | 100 | 0 | 0 |

What is claimed is:

1. A compound having the structural formula Ia

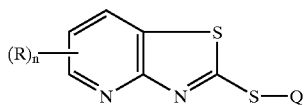

(Ia)

wherein

R is halogen, nitro, cyano, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio or $CO_2R_1$;

n is 0, 1, 2 or 3;

Q is $C_3$–$C_6$haloalkenyl, $C_3$–$C_7$cycloalkyl, $C_3$–$C_7$halocycloalkyl, $C_4$–$C_7$cycloalkenyl, $C_4$–$C_7$halocycloalkenyl, $C_1$–$C_6$alkyl substituted with one $C_3$–$C_7$cycloalkyl or $C_3$–$C_7$halocycloalkyl group, or $C_1$–$C_6$haloalkyl optionally substituted with one $C_3$–$C_7$cycloalkyl or $C_3$–$C_7$halocycloalkyl group, provided that Q is other than $CF_2H$; and $R_1$ is hydrogen, $C_1$–$C_6$alkyl, $CH_2(C_1$–$C_6$haloalkyl), $C_3$–$C_{10}$alkenyl, $C_3$–$C_{10}$haloalkenyl, a cation, benzyl optionally substituted on the ring with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or phenyl optionally substituted with any combination of one to five halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups; or the agriculturally acceptable salt thereof.

2. The compound according to claim 1 selected from the group consisting of

2-[(4,4,3-trifluoro-3-butenyl)thio]thiazolo[4,5-b]pyridine; and

2-[(bromodifluoromethyl)thio]thiazolo[4,5-b]pyridine.

3. 2-[(Difluoromethyl)thio]thiazolo[4,5-b]pyridine.

4. A method for the protection of growing plants from attack or infestation by nematode, insect or acarid pests which comprises applying to the foliage of the plants, or to the soil or water in which they are growing, a pesticidally effective amount of the compound of claim 1.

5. The method according to claim 4 wherein the compound is selected from the group consisting of 2-[(4,4,3-trifluoro-3-butenyl)thio]thiazolo[4,5-b]pyridine;
2-[(bromodifluoromethyl)thio]thiazolo[4,5-b]pyridine; and
2-[(difluoromethyl)thio]thiazolo[4,5-b]pyridine.

6. The method according to claim 4 wherein the pest is a nematode.

7. A composition for the control of helminth, nematode, insect or acarid pests or parasites which comprises an agronomically acceptable carrier, and a pesticidally or parasiticidally effective amount of the compound of claim 1.

8. The composition according to claim 7 wherein said compound is selected from the group consisting of 2-[(4,4,3-trifluoro-3-butenyl)thio]thiazolo[4,5-b]pyridine;
2-[(bromodifluoromethyl)thio]thiazolo[4,5-b]pyridine; and
2-[(difluoromethyl)thio]thiazolo[4,5-b]pyridine.

* * * * *